United States Patent [19]

Schumann

[11] Patent Number: Plant 5,928

[45] Date of Patent: Apr. 7, 1987

[54] GERANIUM PLANT NAMED TWIST

[75] Inventor: Ingeborg Schumann, Bad Ems, Fed. Rep. of Germany

[73] Assignee: Fischer Geraniums, Inc., Netherlands Antilles

[21] Appl. No.: 760,765

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Twist having carmine-salmon flower color; semi-double flower form with large flowerhead; dark green foliage; fast rooting; compact growth habit; and very good chlorophyll quality for transportation.

1 Drawing Figure

The present invention comprises a new and distinct cultivar of geranium, botanically known as *Pelargonium zonale,* and hereinafter referred to by the cultivar name Twist.

Twist is a product of a planned breeding program which had the objective of creating new geranium cultivars having dark green zonated foliage, unique flower color, very good chlorophyll quality for shipping, very fast rooting, and compact growth habit.

Twist was originated from a hybridization made by Ingeborg Schumann in a controlled breeding program in Hillscheid, Federal Republic of Germany in 1981. The female parent was an inbred line of Perlpenie having white, semi-double flowers. The male parent of Twist was Bern, having a red single flower and dark foliage. Bern is a cultivar of the "Pelfi" ® series of Pelargonien-Fischer KG, Hillscheid, Federal Republic of Germany. Both parents are unpatented.

Twist was discovered and selected as one flowering plant within the progeny of the stated cross by Ingeborg Schumann on May 30, 1982 in a controlled environment in Hillscheid, Federal Republic of Germany.

The first act of asexual reproduction of Twist was accomplished when vegetative cuttings were taken from the initial selection in January of 1983 in a controlled environment in Hillscheid, Federal Republic of Germany by a technician working under formulations established and supervised by Ingeborg Schumann. Horticultural examination of selected units initiated in the spring of 1983 and 1984 has demonstrated that the combination of characteristics as herein disclosed for Twist are firmly fixed and are retained through successive generations of asexual reproduction.

Twist has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Twist, which in combination distinguish this geranium as a new and distinct cultivar.

1. Dark green zonated foliage.
2. Carmine-salmon flower color.
3. Semi-double flower form with large flowerhead.

4. Very good chlorophyll quality for transportation.
5. Very fast rooting.
6. Compact growth habit.

The accompanying photographic drawing shows typical flower and foliage characteristics of Twist, with colors being as true as possible with illustrations of this type.

In the following description color references are made to The Royal Horticultural Society Colour Chart. The color values were determined between 10:00 a.m. and 11:00 a.m. on May 22, 1985 under 35,000 Lux light intensity at Hillscheid, Federal Republic of Germany.

Classification:

*Botanical.*—A hybrid of the genus *Pelargonium l'hert* and species *Pelargonium zonale.*

*Commercial.*—Twist.

Inflorescence

A. Umbel:
- *Average diameter.*—114 mm.
- *Average depth.*—62 mm.
- *Peduncle length.*—136 mm.
- *Pedicel length.*—33 mm.

B. Corolla:
- *Average diameter.*—49 mm.
- *Form.*—Semi-double; asymmetric.
- *Color (general tonality from a distance of three meters).*—Carmine-salmon. Upper Surface: 45C.

C. Bud:
- *Shape.*—Oval; pointed.
- *Color.*—White-yellow to light red.

D. Reproductive organs:
- *Androecium.*—5–8 stamens.
- *Gynoecium.*—4–5 lobed stigma.

E. Spring flowering response period: In Hillscheid, Federal Republic of Germany, in 1983, 45% of plants opened with at least one flower 13 weeks after planting of unrooted cuttings.

F. Outdoor flower production: The total flower count in 1983 in Hillscheid, Federal Republic of Germany, was between 46 and 50 flowers per plant for the June through October observation period.

G. Durability: Very good.

PLANT

A. Foliage: Rounded, slightly crenate.
- *Form.*—Kidney shaped.

*Color.*—Top surface: Dark green, near 137A. Zonation: Weak zonation.

*Tolerance of botrytis.*—Good.

B. General appearance and form:

*Internode length.*—21 mm.

*Branching pattern.*—3.0 branches per plant.

*Height.*—200 mm.

I claim:

1. A new and distinct cultivar of geranium named Twist, as described and illustrated, and particularly characterized by its carmine-salmon flower color; semi-double flower form with large flowerhead; dark green foliage; fast rooting; compact growth habit; and very good chlorophyll quality for transportation.

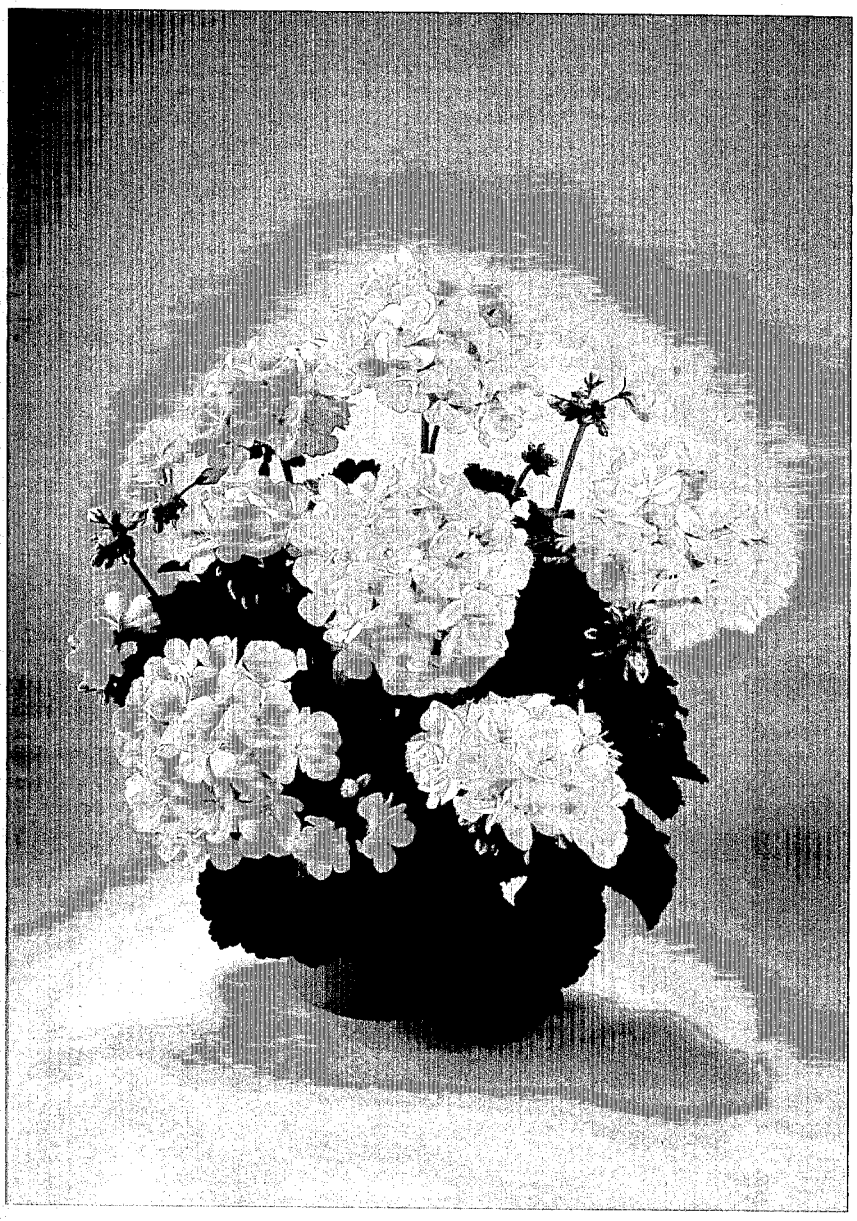

* * * * *